(12) United States Patent
Kretzschmann et al.

(10) Patent No.: US 6,548,462 B1
(45) Date of Patent: Apr. 15, 2003

(54) BISPHENYL THIOCOMPOUNDS

(75) Inventors: Holger Kretzschmann, Rummelsheim (DE); Rudolf Eidenschink, Mainz (DE)

(73) Assignee: Nematel Dr. Rudolph Eidenschink, Mainz (DE)

( * ) Notice: Subject to any disclaimer, the term of this patent is extended or adjusted under 35 U.S.C. 154(b) by 0 days.

(21) Appl. No.: 09/807,646

(22) PCT Filed: Sep. 22, 1999

(86) PCT No.: PCT/DE99/03096

§ 371 (c)(1), (2), (4) Date: Jul. 5, 2001

(87) PCT Pub. No.: WO00/26184

PCT Pub. Date: May 11, 2000

(30) Foreign Application Priority Data

Nov. 3, 1998 (DE) .......................... 198 50 532

(51) Int. Cl.[7] .................. C10M 135/28; C10M 105/72; C07C 321/28

(52) U.S. Cl. .................. 508/569; 508/570; 568/25; 568/58; 44/435

(58) Field of Search ................. 508/569, 570; 568/25, 58

(56) References Cited

U.S. PATENT DOCUMENTS

| | | | | |
|---|---|---|---|---|
| 3,748,269 A | * | 7/1973 | Clark | 252/46.6 |
| 3,844,962 A | * | 10/1974 | Clark | 252/46.7 |
| 4,305,832 A | * | 12/1981 | Braid | 252/48.2 |
| 4,857,572 A | * | 8/1989 | Meier et al. | 524/289 |
| 5,344,577 A | * | 9/1994 | Deckman et al. | 252/45 |
| 5,376,290 A | * | 12/1994 | Meier et al. | 252/47.5 |
| 5,427,701 A | * | 6/1995 | Meier et al. | 252/47.5 |
| 5,998,670 A | * | 12/1999 | Tang et al. | 568/26 |
| 6,001,786 A | * | 12/1999 | Gatto et al. | 508/570 |

FOREIGN PATENT DOCUMENTS

EP 798366 A2 * 10/1997

* cited by examiner

*Primary Examiner*—Ellen M. McAvoy
(74) *Attorney, Agent, or Firm*—Michael L. Dunn

(57) ABSTRACT

The invention relates to bisphenyl thiocompounds of formula (I), wherein $X_1$ to $X_5$ independently represent H, Cl, F, OH, SH, R, —OR and —SR, wherein R is an organic radical with 1 to 18 C atoms, which can be an alkyl or alkenyl radical that can also contain —O—, —S— instead of a one to four non-adjacent $CH_2$ groups and that can be substituted once or multiple times by —OH, —SH or halogen, an unsubstituted phenyl, cyclohexyl or cyclohexylmethyl radical or substituted by one or up to three alkyl groups with a total of 1 to 9 C atoms in which a $CH_2$ group may be replaced by —O—, provided that at least 3 of the radicals $X_1$ to $X_5$ are; $Y_1$ to $Y_5$ independently have the meaning cited for $X_1$ to $X_5$ and Z represents an α, ω-alkylene group with 2 to 18 C atoms in which one to three $CH_2$ groups may be substituted by —O— or —S— and 1,4-cyclohexandimethyl group or a simple bond. The invention also relates to the use of said compounds as lubricants.

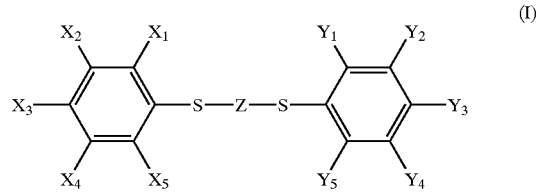

16 Claims, No Drawings

BISPHENYL THIOCOMPOUNDS

The invention relates to novel bisphenylthio compounds and their use as lubricants.

In order to reduce the wear and the energy loss due to friction, machine bearings and gears are known to be provided with a lubricant which, during operation, permits as complete separation as possible of the solid bodies moving against one another. The lubricants may be divided into lubricating liquids and lubricating greases. Conventional lubricating liquids in use are mineral oils obtained from petroleum, synthetic oils, such as polyalkylene glycols, ethylene polysulphides, ester oils or phosphoric acid esters, and silicone oils (Ullmann's Encyclopedia of Industrial Chemistry, 5th Edition, Vol. A15, page 423 et seq., VCH Weinheim 1990). Mesogenic liquids, i.e. liquids which form thermotropic liquid crystalline phases and can be; transformed from a low-viscosity into a high-viscosity phase, and vice versa, in the lubricating gap (U.S. Pat. No. 5,160,451) are also known. In general, a liquid is referred to as mesogenic if it can form one or more liquid crystalline phases under specific conditions (pressure, temperature, shearing, surface interactions). The relationships between chemical structure and the arrangement of the molecules in such phases and the temperature range in which such phases can occur is known (e.g. H. Kelker, R. Hatz, Handbook of Liquid Crystals, Verlag Chemie, Weinheim 1980; C. Destrade et al., Mol. Cryst. Liq. Cryst. Vol. 106, 121 (1984). Lubrication with lubricating greases is widely used. These lubricating greases consist of a lubricating liquid and, dispersed therein in fine form, a solid, the so-called thickener which has only a slight effect on the tribological properties and is primarily a reservoir for the lubricating liquid. In addition, very low-viscosity organic substances, such as fuels for spark-ignition engines (petrol) and diesel engines (diesel fuel), can also be considered as lubricants, which is clear from the known effect of the fuel on the wear of nozzle valves of fuel injection nozzles. Solutions and emulsions of organic compounds in water also serve as lubricants, in particular as so-called cooling lubricants in the machining of metallic workpieces.

The energy losses and wear phenomena occurring in a friction pairing—these are generally solid bodies separated by a lubrication gap and moving against one another—depend in a complex manner on the material of the machine element itself, on the properties of the lubricating oil, such as its viscosity and its interactions with the material, and on the pressure and velocity conditions. Continuous supporting films, as occur, for example, in the hydrodynamic region of sliding bearing or in the elastohydrodynamic region of roller bearings, are advantageous. High frictional losses, characterized by the generally customary coefficients of friction, and the wear phenomena generally correlated with them occur particularly in sliding bearings in the case of so-called boundary friction and mixed friction (cf. Ullmann's Encycl.).

In addition to the ethylene polysulphides, inter alia hexakis-, pentakis- and tetrakis[alkylthio]benzenes are known as sulphur-containing lubricants (DE 196 11 466). The latter compounds are distinguished by particularly good lubricating properties. Owing to their tendency to form discotic phases under atmospheric pressure at temperatures as low as in the range from 0 to –10° C., and in particular such phases which are characterized by a particularly high degree of ordering of the molecules and very high viscosities, these lubricants are not suitable for machine bearings which have to be supplied with a liquid medium at temperatures down to –40° C. by a continuous flow process.

It was an object of the invention to provide sulphur compounds which have the advantageous frictional and wear properties of the above-mentioned alkylthiobenzenes but, even at low temperatures, exhibit no transition to a liquid crystalline phase disadvantageous for the flowability.

The object was achieved by providing the compounds, according to the invention, of the general formula I

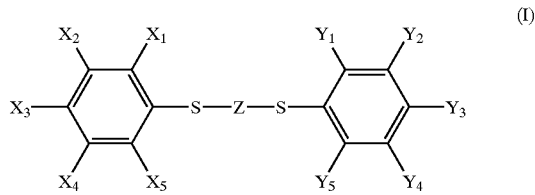

in which $X_1$ to $X_5$ in each case independently of one another represents H, Cl, F, OH, SH, R, —OR and —SR, R being an organic radical having 1 to 18 C atoms which may be an alkyl or alkenyl radical which may also contain —O— or —S— instead of one to four non-neighbouring $CH_2$ groups and may also be monosubstituted or polysubstituted by —OH, —SH or halogen, or a phenyl, cyclohexyl or cyclohexylmethyl radical which is unsubstituted or substituted by one to 3 alkyl groups having a total of 1 to 9 C atoms, in which in each case a $CH_2$ group may be replaced by —O—, with the proviso that at least 3 of the radicals $X_1$ to $X_5$ are —SR, $Y_1$ to $Y_5$ in each case independently of one another have the meaning stated for $X_1$ to $X_5$ and z denotes an α,ω-alkylene group having 2 to 18 C atoms in which one to 3 $CH_2$ groups may also be replaced by —O— or —S—, or a 1,4-cyclohexanedimethyl group

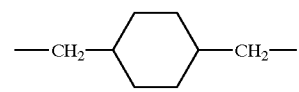

or a single bond.

It was found that the compounds according to the invention are suitable as lubricants which permit particularly small frictional losses in friction pairings and surprisingly are flowable at low temperatures.

The molecules of the compounds of the formula I contain two phenyl rings which are linked via a bridge containing at least two S atoms. Altogether, at least 8 S atoms are contained in the molecule, each phenyl ring being linked to at least 4 S atoms. Preferred compounds are those in which both phenyl groups are each linked to at least 5 S atoms, particularly preferably those in which both phenyl groups are each linked to 6 S atoms.

The substituents $X_1$ to $X_5$ and, in each case independently of one another, $Y_1$ to $Y_5$ are preferably —SR, —H or —SH. The radical R preferably designates an alkyl radical having 1 to 18 C atoms, in which one to four nonneighbouring $CH_2$ groups may also be replaced by —O— or —S— and which may be substituted by —OH or —SH. Straight alkyl chains are particularly preferred, very particularly those having 6 to 12 C atoms.

The group Z preferably contains 2 to 10 C atoms. Particularly preferred here are straight-chain α,ω-alkylene groups. The 1,4-clohexanedimethyl group is also preferred.

The formulae Ia to If are examples of compounds according to the invention:

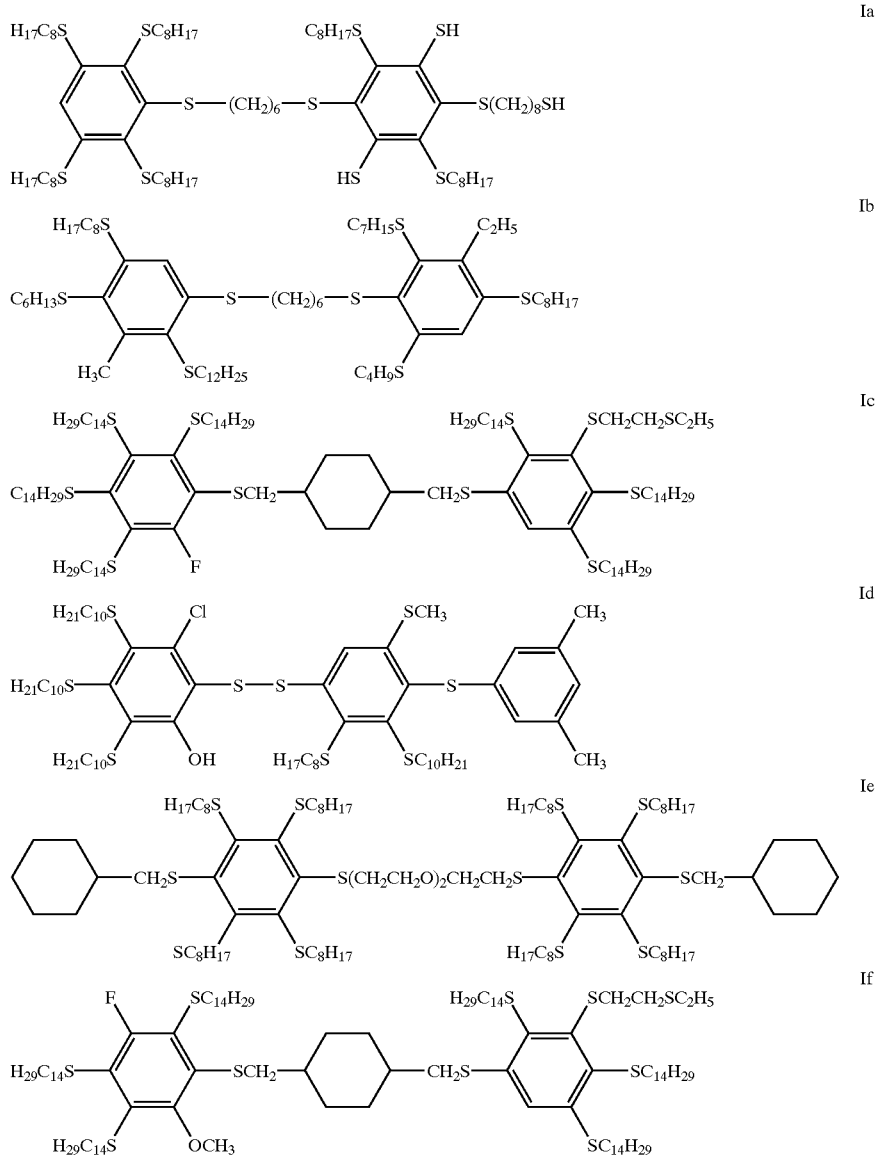

The preparation of the compounds of the formula I is carried out by generally known methods of synthetic chemistry, as described, for example, in R. C. Larock, Comprehensive Organic Transformations, VCH Publishers, Inc. (1989) and in Houben-Weyl, Methoden der Organischen Chemie [Methods of Organic Chemistry], Georg-Thieme Verlag, Stuttgart.

Compounds of the formula I are preferably prepared by first producing, from a mixture of the thiols RSH and HS—Z—SH, in an aprotic solvent, such as N-methyl-2-pyrrolidinone, N,N-dimethylformamide or tetramethyleneglycol dimethyl ether, by reaction with sodium amide or sodium hydride, the corresponding sodium thiolates, which are then converted into mixtures of compounds of the formula I by addition of halobenzenes, such as hexa-, penta- or tetrachlorobenzene, or the corresponding fluorine compounds, in a substitution reaction at temperatures between 50° C. and 180° C.

If mixtures of the thiols RSH, such as, for example, mixtures selected from the compounds octadecylthiol, hexadecylthiol, tetradecylthiol, dodecylthiol, decylthiol, nonylthiol, octylthiol, heptylthiol, hexylthiol, pentylthiol, butylthiol, propylthiol, ethylthiol and methylthiol, are used, mixtures of numerous compounds of the formula I with a randomly distributed arrangement of the various substituents RS are formed. By selecting the alkyl chain length of the thiols used and their proportions, it is possible to influence the viscosity and flow behaviour at low temperatures.

If, in the reactions mentioned, less than the stoichiometric amount of metal thiolates is chosen, compounds of the formula I having halogen substituents can be obtained.

The introduction of the —SZS— bridge can also be effected by reaction of phenylthiols with dihaloalkanes in aprotic solvents with the addition of bases, e.g.

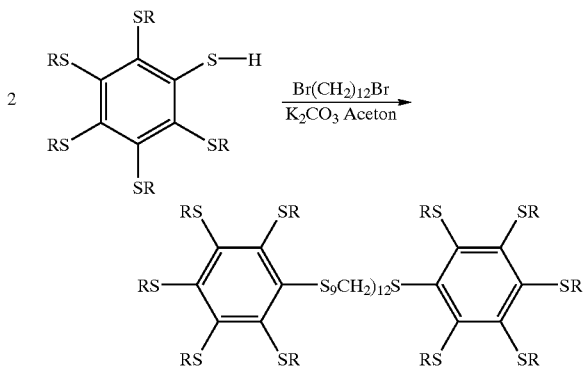

Preferred dihalo compounds are 1,4-dibromobutane, 1,6-dibromohexane, 1,8-dibromooctane, 1,12-dibromododecane and 1,4-bis[bromomethyl]cyclohexane. By known oxidation reactions, substituted diphenyl disulphides of the formula I (Z is a single bond) can be obtained from the above-mentioned phenylthiols.

After the substitution reaction is complete and the solvent has been distilled off, dilute hydrochloric acid is added to the distillation residue. The organic phase which separates from the aqueous phase contains compounds of the formula I in addition to compounds of the formula II in which the radicals $X_1$ to $X_5$ have the above-mentioned meanings.

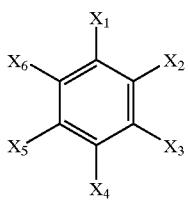

II

The additional substituent $X_6$ may have one of these meanings may be —SZSH and, where Z is an alkylene group, also —SZCl or —SZBr. In addition, a small amount of compounds of the formula III are formed, which have the following general structural formula

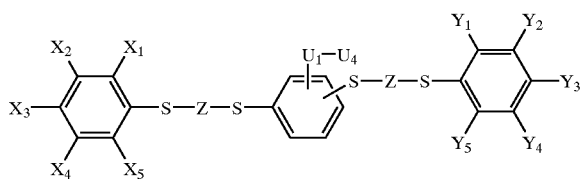

III

In formula III, the middle phenyl ring can be substituted by the two bridge groups in the ortho, meta or para position. Groups $U_1$ to $U_4$ have the meaning as stated above under $X_1$ to $X_5$.

The compounds of the general formulae II and III are as a rule not removed from the mixture for the intended use as a lubricant. Rather, it may be regarded as a fortunate circumstance that these substances also have advantageous lubricating properties. However, the compounds of the formula I can be isolated by chromatographic methods.

The lubricant according to the invention contains 1 to 100, preferably 1 to 60 and very preferably 5 to 40, percent by mass of compounds of the formula I.

The content of compounds of the formula I in the lubricant according to the invention is expediently determined by the generally known method of gel permeation chromatography (GPC). For identification of the compounds, the known field desorption mass spectroscopy (FD-MS) is advantageously used. It is possible to carry out an assay using this mass spectroscopic method alone, because only the masses of the molecular ions are indicated in the spectra. In this case, the use of calibration substances is necessary.

It was found that the compounds, according to the invention, of the formula I are suitable as lubricants. Compared with conventional lubricants, they permit substantially lower frictional losses in gears and bearings.

The lubricants to which the invention relates may contain exclusively compounds of the formula I. As a rule, however, compounds of the formulae II and III and further components are present. Such components may be, inter alia, antioxidants, such as derivatives of 2,6-di-tert-butylphenol, high-pressure additives, such as zinc dialkyl dithiophosphates, friction-reducing substances, light stabilizers, emulsifiers or demulsifiers. However, organic compounds for varying the viscosity, such as compounds whose molecules contain benzene or naphthalene nuclei polysubstituted by alkyl groups, may also be present. The invention also relates to those lubricants whose main proportion (up to 99 percent by mass) comprise conventional synthetic or mineral oils (cf. Ullmann's Encycl.). If the lubricant according to the invention is a lubricating oil, all components are present in molecular disperse form in the homogeneous liquid.

Oil-like lubricants can be converted in a generally known manner (cf. Ullmann's Encycl.) into a lubricating grease by adding thickeners which are not present in molecular disperse form. Particularly suitable thickeners are lithium 12-hydroxystearate and polytetrafluoroethylene powders (e.g. 5 μm microteflon powder, Dr. Tillwich GmbH, Horb). The present invention also includes among the thickeners polymers which serve for the formation of gels, such as, for example, so-called side-chain polymers (H. Ringsdorf et al., Angew. Chem. 101, 934 (1989) and literature cited there), as well as inorganic solid additives, such as molybdenum sulphide or graphite. Such lubricant greases which contain one or more compounds of the formula I and which may contain up to 35% of such thickeners are to be regarded here as lubricants according to the invention.

The invention also relates to so-called cooling lubricants, which are emulsions of organic lubricating oils in aqueous solutions. That fraction of a cooling lubricant which can be isolated as a homogeneous nonaqueous phase from the emulsion by known methods of demulsification, such as ultracentrifuging, salting out or addition of demulsifiers, is regarded as a lubricant according to the invention.

The lubricants according to the invention are distinguished by good continuous flow behaviour at low temperatures. This is advantageous for the trouble-free operation of machine bearings and in particular of gears. In order to assess the continuous flow behaviour of lubricants at low temperatures, the so-called channelling test (Federal Test Method Std. No. 791C, USA) is used: about 600 ml of lubricants are cooled for 18 to 20 hours at the desired test temperature in a container having a diameter of 90 mm and a height of 100 mm. A 20 mm wide furrow is then drawn through the sample with a sheet steel strip (230×20 mm, thickness 3 mm). If the lubricant flows back within 10 seconds so that the bottom of the container is covered again, the lubricant has flowability adequate for gears.

The following examples are intended to illustrate the invention without limiting it.

EXAMPLE 1

100.8 g (4.20 mol) of sodium hydride and 1.1 of tetraethylene glycol dimethyl ether are introduced under nitrogen into a 6 three-necked flask having a dropping funnel and KPG stirrer and are vigorously stirred at room temperature. A mixture of 50.0 g (0.33 mol) of 1,6-dimercaptohexane and 486.7 g (3.33 mol) of n-octyl mercaptan is rapidly added dropwise. During this procedure, the temperature increases to about 50° C. After the addition is complete, vigorous stirring is continued for a further 20 min. 379.0 g (1.33 mol) of hexachlorobenzene are then added in portions, the internal temperature increasing further and the white, viscous slurry slowly becoming yellow. After the addition is complete, an oil bath is pushed underneath and the mixture is heated to 130° C. for 3 h with vigorous stirring. 122.2 g (5.05 mol) of sodium hydride in 1.4 of tetraethylene glycol dimethyl ether are initially introduced into a separate flask having a bottom discharge, and 700.0 g (4.78 mol) of n-octyl mercaptan are rapidly added dropwise with vigorous stirring. After the addition is complete, stirring is continued for a further 15 min and the mixture at 50° C. is allowed to run into the 6 l flask. The viscous mixture is then heated to 130° C. for a further 24 h, the white precipitate dissolving and the mixture becoming yellow. The solvent is removed in vacuo (oil pump) (top temperature 115° C.), the residue is left to cool and 1000 ml of petroleum ether and 1 l of dilute hydrochloric acid are added and thorough stirring is carried out. The phases are separated and the organic phase is extracted by shaking three times with 300 ml portions of concentrated sodium chloride solution and several times with water. The organic phase is dried with sodium sulphate, filtered and evaporated in a rotary evaporator. 1362 g of crude product which still contains volatile fractions are obtained. After these have been distilled off under a vacuum from an oil pump (0.1 mbar), 1116 g of a brown oil remains.

According to GPC chromatography and FD mass spectroscopic identification (isotope pattern of the molecular peak corresponds to the empirical formula $C_{98}H_{182}S_{12}$), the amount of 1,6-bis{pentakis[octylthio]phenylthio}hexane herein is 15%; the main proportion is hexakis[octylthio]benzene. The viscosity of the product at 40° C. is 86 $mm^2/s$. In a standardized vibratory frictional wear test (SRV brochure, Optimol Prüftechnik GmbH, Munich) with a steel cylinder (diameter 15 mm, length 22 mm; load 50 N, amplitude 1 mm, frequency 50 Hz, 80° C., duration 10 h) oscillating on a steel disc (diameter 24 mm), this oil showed substantially lower coefficients of friction than a conventional mineral lubricating oil of the same viscosity. The flowability according to the above-mentioned channelling test is present at —25° C. Pure hexakis[octylthio]benzene is no longer flowable below −10° C. according to this test.

EXAMPLE 2

Analogously to Example 1, a solution of hexakis[octylthio]benzene and excess sodium octyl thiolate is prepared from 120.7 g (8.78 mol) of sodium hydride, 2.5 of tetraethylene glycol dimethyl ether, 1240 g (8.38 mol) of octanethiol and 379.0 g (1.33 mol) of hexachlorobenzene. By stirring for 3 days under nitrogen at 140° C., a part of the product is converted into pentakis[octylthio]-thiobenzene by dealkylation (cf. S. D. Pastor, E. T. Hessel, J. Org. Chem. 50, 4812 (1985)). After the solvent has been distilled off, working up is carried out in the manner described in Example 1. According to FD-MS, the resulting oil (1155 g) contains 32% of pentakis[octylthio]-thiobenzene. The oil is dissolved together with 50.0 g of 1,6-dibromohexane in 3 l of acetone. After the addition of 230 g of potassium carbonate, stirring is carried out for 24 h at room temperature, the suspension is filtered and the filtrate is concentrated by evaporation. Volatile impurities are removed in vacuo (0.1 mbar) at a bottom temperature of 190° C. The oil (1170 g) contains 30% of 1,6-bis{pentakis[octylthio]phenylthio}hexane. Its viscosity at 40° C. is 171 $mm^2/s$. The flowability according to the above-mentioned channelling test is present at −40° C. From 10 g of the oil, 2.0 g of the bisphenylthiohexane according to the invention are obtained as a highly viscous yellow oil by separation by column chromatography (silica gel/petroleum ether-toluene mixture).

EXAMPLE 3

An oil containing 32 percent by mass of pentakis[octylthio]thiobenzene is prepared as described in Example 2. 120 g of this oil are dissolved together with 5.3 g of the known trans-1,4-bis[bromomethyl]cyclohexane in 300 ml of acetone and, after the addition of 23.0 g of potassium carbonate, are reacted and further processed as described. From the product, trans-1,4-bis{pentakis[octylthio](phenylthio)methyl}cyclohexane can be isolated as a highly viscous yellow oil by the chromatographic separation method described.

What is claimed is:
1. A compound of the general formula I:

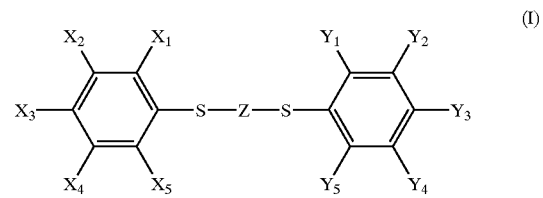

in which $X_1$ to $X_5$ in each case independently of one another represents H, Cl, F, OH, SH, R, —OR and —SR, R being an organic radical having 1 to 18 C atoms which may be an alkyl or alkenyl radical which may also contain —O— or —S— instead of one to four non-neighbouring $CH_2$ groups and may also be monosubstituted or polysubstituted by —OH, —SH or halogen, or a phenyl, cyclohexyl or cyclohexylmethyl radical which is unsubstituted or substituted by one to 3 alkyl groups having a total of 1 to 9 C atoms, in which in each case a $CH_2$ group may be replaced by —O—, with the proviso that at least 3 of the radicals $X_1$ to $X_5$ are —SR, $Y_1$ to $Y_5$ in each case independently of one another have the meaning stated for $X_1$ to $X_5$ and Z denotes an α,ω-alkylene group having 2 to 18 C atoms in which one to 3 $CH_2$ groups may also be replaced by —O— or —S—, or a 1,4-cyclohexanedimethyl group

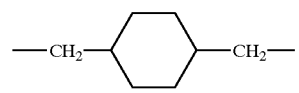

or a single bond.

2. A compound according to claim 1 of the general formula:

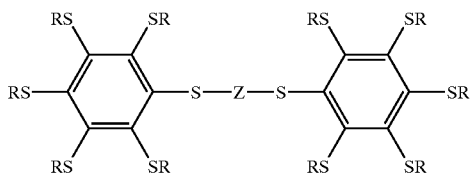

in which Z denotes an α,ω-alkylene group having 2 to 18 C atoms, in which 1 to 3 CH$_2$ groups may be replaced by —O—.

3. A compound according to claim 2 of the general formula:

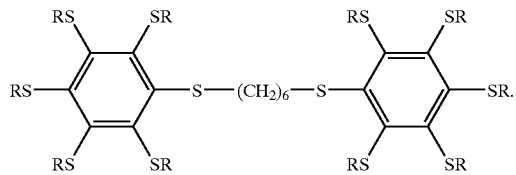

4. A compound according to claim 1 of the general formula:

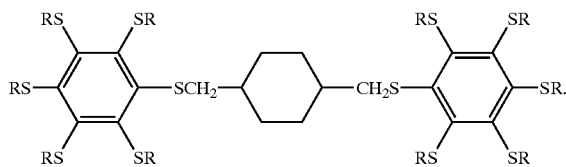

5. A lubricant composition containing from 1 to 100 percent by mass of a compound of claim 1 and from 0 to 99 percent by mass of an organic lubricant selected from the group consisting of mineral oils, synthetic oils, greases, polyalkylene glycol, ethylene polysulfide, hexakis(alkylthio)benzene, pentakis(alkylthio)benzene, tetrakis(alkylthio)-benzene, organic acid esters, phosphoric acid esters, silicone oils, organic fuels, mixtures thereof and aqueous emulsions thereof.

6. A lubricant composition containing from 1 to 100 percent by mass of a compound of claim 2 and from 0 to 99 percent by mass of an organic lubricant selected from the group consisting of mineral oils, synthetic oils, greases, polyalkylene glycol, ethylene polysulfide, hexakis(alkylthio)benzene, pentakis(alkylthio)benzene, tetrakis(alkylthio)-benzene, organic acid esters, phosphoric acid esters, silicone oils, organic fuels, mixtures thereof and aqueous emulsions thereof.

7. A lubricant composition containing from 1 to 100 percent by mass of a compound of claim 3 and from 0 to 99 percent by mass of an organic lubricant selected from the group consisting of mineral oils, synthetic oils, greases, polyalkylene glycol, ethylene polysulfide, hexakis(alkylthio)benzene, pentakis(alkylthio)benzene, tetrakis(alkylthio)-benzene, organic acid esters, phosphoric acid esters, silicone oils, organic fuels, mixtures thereof and aqueous emulsions thereof.

8. A lubricant composition containing from 1 to 100 percent by mass of a compound of claim 4 and from 0 to 99 percent by mass of an organic lubricant selected from the group consisting of mineral oils, synthetic oils, greases, polyalkylene glycol, ethylene polysulfide, hexakis(alkylthio)benzene, pentakis(alkylthio)benzene, tetrakis(alkylthio)-benzene, organic acid esters, phosphoric acid esters, silicone oils, organic fuels, mixtures thereof and aqueous emulsions thereof.

9. A method for lubricating a surface comprising coating the surface with the lubricant composition of claim 5.

10. A method for lubricating a surface comprising coating the surface with the lubricant composition of claim 6.

11. A method for lubricating a surface comprising coating the surface with the lubricant composition of claim 7.

12. A method for lubricating a surface comprising coating the surface with the lubricant composition of claim 8.

13. A method for lubricating a surface comprising coating the surface with the compound of claim 1.

14. A method for lubricating a surface comprising coating the surface with the compound of claim 2.

15. A method for lubricating a surface comprising coating the surface with the compound of claim 3.

16. A method for lubricating a surface comprising coating the surface with the compound of claim 4.

* * * * *